United States Patent
Kinugawa et al.

(10) Patent No.: US 9,341,566 B2
(45) Date of Patent: May 17, 2016

(54) RESIN TYPE IDENTIFICATION METHOD AND RESIN TYPE IDENTIFICATION APPARATUS

(71) Applicants: Mitsubishi Electric Corporation, Chiyoda-ku (JP); Shimadzu Corporation, Kyoto-shi (JP)

(72) Inventors: Masaru Kinugawa, Chiyoda-ku (JP); Muneaki Mukuda, Chiyoda-ku (JP); Sonoko Umemura, Chiyoda-ku (JP); Yasuyuki Nakagawa, Chiyoda-ku (JP); Naoji Moriya, Nara (JP); Toru Yamaguchi, Soraku-gun (JP); Yukihisa Wada, Soraku-gun (JP)

(73) Assignees: Mitsubishi Electric Corporation, Chiyoda-ku (JP); Shimadzu Corporation, Kyoto-shi (JP)

( * ) Notice: Subject to any disclaimer, the term of this patent is extended or adjusted under 35 U.S.C. 154(b) by 198 days.

(21) Appl. No.: 14/156,728

(22) Filed: Jan. 16, 2014

(65) Prior Publication Data
US 2014/0203177 A1    Jul. 24, 2014

(30) Foreign Application Priority Data

Jan. 21, 2013 (JP) ................................. 2013-008558
Aug. 7, 2013 (JP) ................................. 2013-164339

(51) Int. Cl.
| | | |
|---|---|---|
| G01J 5/02 | (2006.01) | |
| G01N 21/3563 | (2014.01) | |
| B29B 17/02 | (2006.01) | |
| G01N 21/552 | (2014.01) | |

(52) U.S. Cl.
CPC ............ *G01N 21/3563* (2013.01); *B29B 17/02* (2013.01); *B29B 2017/0279* (2013.01); *G01N 21/552* (2013.01); *Y02W 30/622* (2015.05)

(58) Field of Classification Search
CPC .. G01N 33/442; G01N 21/65; G01N 21/3563
USPC .............................. 250/339.11, 339.08, 341.8
See application file for complete search history.

(56) References Cited

U.S. PATENT DOCUMENTS

| | | | | |
|---|---|---|---|---|
| 5,141,110 A | * | 8/1992 | Trischan ............... | B07C 5/3416 209/3.1 |
| 7,842,896 B1 | * | 11/2010 | Calcoen ................ | B07C 5/3427 209/576 |

(Continued)

FOREIGN PATENT DOCUMENTS

| | | |
|---|---|---|
| JP | 2010-110733 | 5/2010 |
| JP | 2010-207772 | 9/2010 |

(Continued)

OTHER PUBLICATIONS

Translation of international patent application publiction No. WO/2012/120779 of Oota et al.*
Masaru Kinugawa, et al., "Identification of post-consumer plastics flakes by IR reflectivity method", Preprints of Seikei-Kakou Annual Meeting 2012, Jun. 12-13, 2012, 3 pages.

*Primary Examiner* — David J Makiya
*Assistant Examiner* — Kenneth J Malkowski
(74) *Attorney, Agent, or Firm* — Oblon, McClelland, Maier & Neustadt, L.L.P

(57) ABSTRACT

To obtain a resin type identification method and a resin type identification apparatus with which an optimum infrared reflection spectrum for identifying a resin piece can be selected and accurate identification processing can be performed successively on individual resin pieces even when the resin pieces are identified using a single optical detector, at least one identifying signal power is selected by executing signal processing on the basis of signal powers corresponding to infrared reflection intensities obtained by emitting infrared light onto the resin piece, and the resin type of the resin piece is identified on the basis of an infrared reflection spectrum corresponding to the selected identifying signal power.

21 Claims, 5 Drawing Sheets

(56) References Cited

U.S. PATENT DOCUMENTS

2001/0054900 A1* 12/2001 Yokoyama ............ G01N 33/442
                                                    324/453
2002/0062844 A1*  5/2002 Imai .................... B02C 18/0076
                                                    134/18

FOREIGN PATENT DOCUMENTS

| JP | 2012-103026 | 5/2012 | |
| JP | 2012-145528 | 8/2012 | |
| WO | WO 2012/063535 A1 | 5/2012 | |
| WO | WO 2012120779 A1 * | 9/2012 | .............. B29B 17/02 |

* cited by examiner

RESIN TYPE IDENTIFICATION METHOD AND RESIN TYPE IDENTIFICATION APPARATUS

BACKGROUND OF THE INVENTION

1. Field of the Invention

The present invention relates to resin recycling, and more particularly to a resin type identification method and a resin type identification apparatus featuring a method of selecting an infrared reflection spectrum to be used when recycled resin is identified according to composition using an optical method.

2. Description of the Related Art

When resin from used household appliances is recycled, parts in which the resin can be dismantled by hand are limited. Therefore, small components, components having a complicated configuration, and so on must be pulverized by machine and then sorted into metal, resin, and so on in order to be turned into recycled material.

In this case, the respective materials must be separated from a pulverized, intermixed condition, and therefore a sophisticated sorting technique is required. Metal is sorted by specific gravity or using electric or magnetic force. Resin, however, cannot be sorted using electric or magnetic force, and therefore classification according to specific gravity, electrostatic charge, and so on has been proposed.

However, it is difficult to identify similar types of resin using these methods. Hence, an identification method that focuses on differences in an absorptivity or a wavelength (wave number) dependence of a reflectance of the resin in relation to light in a near-infrared band or a mid-infrared band has been proposed.

Here, when black resin containing carbon black or the like is identified, a large amount of absorption occurs in the near-infrared band, and therefore a required signal strength cannot be obtained, making identification difficult. Hence, to identify black resin, it is preferable to use the mid-infrared band, which is less affected by the absorption of the carbon black.

In a method (an infrared spectroscopy method) of identifying individual pulverized resin pieces using the mid-infrared band, samples are conveyed in succession by a conveyor, and the samples are measured from above by a reflection method using FT-IR (Fourier Transform-Infrared Spectroscopy) (see Japanese Patent Application Publication No. S60-089732 and Japanese Patent Application Publication No. H8-300354, for example).

Note that typically, when identifying resin pieces using FT-IR, positioning between a measurement optical system and a measurement subject resin piece (to be referred to hereafter simply as "positioning") must be performed with a high degree of precision to ensure that a measurement region of the measurement optical system is positioned on a surface of the measurement subject resin piece (to be referred to hereafter as "sample").

The reason for this is that when the position of the sample is offset, a proportion of the measurement region occupied by the sample decreases, leading to a reduction in an infrared reflection intensity from the sample and intermixing of infrared reflection from a sample stage. Furthermore, as a result, an S/N ratio (a magnitude of noise relative to a peak height generated by the resin) of an infrared reflection spectrum generated by the sample decreases, and therefore the resin piece cannot be identified accurately.

More specifically, a size of the measurement region when FT-IR is performed using a specular reflection method or a diffuse reflection method is typically between approximately several mm and 1 cm. Therefore, when the size of the sample is equal to or smaller than 1 cm, an offset of several mm in the sample leads to an error during identification of the resin piece. Note that the size of the measurement region is dependent on a size of a light source, a size of a light reception unit of a detector, and the optical system.

However, following problems arise in the related art.

When, in the identification method using FT-IR according to the related art described in Japanese Patent Application Publication No. S60-089732 and Japanese Patent Application Publication No. H8-300354, a plurality of samples are separated and conveyed individually through the optical measurement system, it is impossible to identify resin pieces accurately unless the individual samples are positioned with a high degree of precision.

In the related art, it is difficult to convey the samples individually when the samples are smaller than the measurement region. It is also difficult to position the individual samples in a short amount of time. As a result, a large amount of time is required to identify the resin pieces accurately.

Further, in an identification method using near-infrared light or Raman light, a plurality of array sensors are arranged in a single row, and therefore the need for positioning can, in effect, be eliminated. In the identification method using FT-IR, however, an interference optical system is used, making it more difficult to arrange a plurality of detectors in a single row than with an identification method using near-infrared light or Raman light.

Hence, the following three methods are typically cited as methods of positioning samples using a single detector.

(1) A method of moving individual samples to a measurement region range by adjusting each sample in two directions, namely an X direction and a Y direction.

(2) A method of adjusting the individual samples only in the Y direction and then moving each sample in the X direction using a conveyor belt or the like so that the sample arrives at the measurement region range at a predetermined timing.

(3) A method of moving the individual samples in the X direction and the Y direction so that each sample arrives at the measurement region range at a predetermined timing.

Here, the method of (1) is the most suitable method for shortening a time interval between the end of measurement of one sample and the start of measurement of the next sample. However, a large-scale device is required to adjust samples having different shapes and sizes in two directions, i.e. the X direction and the Y direction. Further, in the method of (3), the time interval is longest, and therefore efficiency is poorest.

Hence, in an example of a specific operation executed when positioning is performed using the method of (2), a plurality of samples are carried on a metallic moving stage (or a conveyor belt or the like) so as not to overlap and moved in succession, and the samples are aligned by a position adjustment rail or the like disposed in a perpendicular direction to a movement direction of the samples, for example. A timing at which each sample arrives at the measurement range is detected by a position sensor or the like, and measurement is performed at this timing.

In another example of a specific operation, an identification unit performs measurement while the aligned samples move, regardless of whether or not a sample is present, whereby infrared reflection spectra are obtained continuously at fixed intervals. One or a plurality of infrared reflection spectra including an infrared reflection signal from a sample are then selected from the obtained infrared reflection spectra, whereupon the selected infrared reflection spectrum is used to identify the resin piece.

When a plurality of small resin pieces are identified automatically in succession, it is difficult to position the individual resin pieces, and therefore the latter method is preferable. With the latter method, however, in which one or a plurality of infrared reflection spectra is selected, it has not been possible up to the present to clarify a reference on the basis of which to select an optimum spectrum for identifying the resin pieces, and therefore, when an infrared reflection spectrum which is unsuitable for identification is selected, identification cannot be performed accurately, leading to a determination error.

Here, when a spectrum simply having a high infrared reflection intensity is selected, the selected spectrum may be a spectrum having a poor S/N ratio due to intermixing of a strong reflection spectrum from the moving stage, and in this case, accurate identification is difficult. When, on the other hand, a spectrum having the lowest infrared reflection intensity is selected to avoid selection of a spectrum intermixed with an infrared reflection spectrum from the moving stage, the intensity of the selected spectrum may be too low, making accurate identification difficult.

SUMMARY OF THE INVENTION

The present invention has been designed to solve these problems, and an object thereof is to obtain a resin type identification method and a resin type identification apparatus with which an optimum infrared reflection spectrum for identifying a resin piece can be selected and accurate identification processing can be performed in succession on individual resin pieces even when the resin pieces are identified using a single optical detector.

A resin type identification method according to the present invention is used to identify a resin type of resin pieces conveyed in succession to a measurement range by having a controller execute signal processing on the basis of time-series signal powers corresponding to infrared reflection intensities obtained by emitting infrared light onto the measurement range at predetermined time intervals. The controller implements: a selection step of selecting at least one identifying signal power for identifying the resin type of the resin pieces from the time-series signal powers corresponding to measurement position of the each resin piece conveyed in succession, on the basis of respective magnitudes of the time-series signal powers; and an identification step of identifying the resin type of the resin pieces on the basis of an infrared reflection spectrum corresponding to the selected identifying signal power.

A resin type identification apparatus according to the present invention includes: an infrared spectroscopy device that obtains time-series signal powers corresponding to infrared reflection intensities by emitting infrared light onto a measurement range at predetermined time intervals; a conveyor that conveys resin pieces in succession to the measurement range of the infrared spectroscopy device; and a controller that identifies a resin type of the resin pieces conveyed by the conveyor in succession to the measurement range, by executing signal processing on the basis of the time-series signal powers corresponding to the infrared reflection intensities received from the infrared spectroscopy device, wherein the controller selects at least one identifying signal power for identifying the resin type of the resin pieces from the time-series signal powers corresponding to measurement position of the each resin piece conveyed in succession, on the basis of respective magnitudes of the time-series signal powers, and identifies the resin type of the resin pieces on the basis of an infrared reflection spectrum corresponding to the selected identifying signal power.

According to the present invention, at least one identifying signal power is selected by executing signal processing on the basis of the signal powers corresponding to the infrared reflection intensities obtained by emitting infrared light onto the resin pieces, and the resin type of the resin pieces is identified on the basis of the infrared reflection spectrum corresponding to the selected identifying signal power. As a result, it is possible to obtain a resin type identification method and a resin type identification apparatus with which an optimum infrared reflection spectrum for identifying a resin piece can be selected and accurate identification processing can be performed in succession on individual resin pieces even when the resin pieces are identified using a single optical detector.

DETAILED DESCRIPTION OF THE PREFERRED EMBODIMENT

Figure 1:
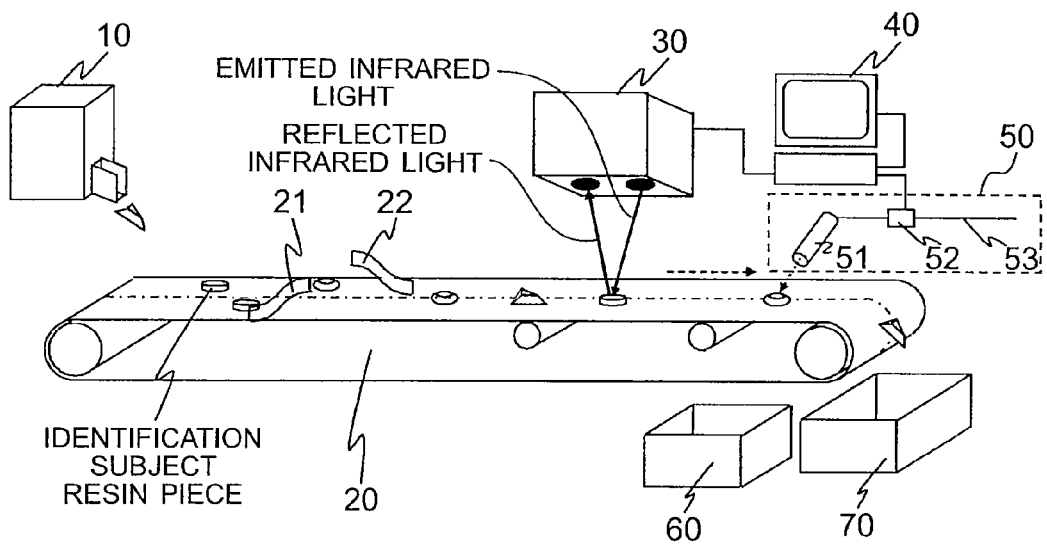
FIG. 1 is an overall view of a resin type identification apparatus according to a first embodiment of the present invention.

Preferred embodiments of a resin type identification method and a resin type identification apparatus will be described below using the drawings. Note that in the description of the drawings, identical reference numerals have been allocated to identical elements, and duplicate description thereof has been omitted.

First Embodiment

FIG. 1 is an overall view of a resin type identification apparatus according to a first embodiment of the present invention. A resin type identification apparatus according to the first embodiment includes a supply device 10, a conveyor 20, an infrared spectroscopy device 30, a controller 40, a resin piece separating device 50, a foreign substance collection container 60, and a resin piece collection container 70. Here, FT-IR is applied as the infrared spectroscopy device 30.

The conveyor 20 includes a first guide 21 and a second guide 22 provided to align conveyed resin pieces. The resin piece separating device 50 includes an air gun 51, an air valve 52, and an air pipe 53, wherein the air gun 51 and the air valve 52 are connected to the air pipe 53.

The supply device 10 supplies identification subject resin pieces onto the conveyor 20 in succession. Further, when the resin pieces are supplied onto the conveyor 20, the individual resin pieces are arranged via gaps so as not to overlap.

An interval of the gap may be fixed or unfixed. Further, as described in Japanese Patent Application Publication No. 2002-131310, for example, flattening processing using a hot press or the like may be implemented in advance on the identification subject resin piece before being supplied onto the conveyor 20 to form a flat portion on a surface of the resin piece. Furthermore, a metal that does not easily absorb infrared light is more preferably used as a specific material of the conveyor 20 than an organic substance such as rubber that absorbs infrared light easily. In other words, the conveyor 20 is preferably constituted by a material having a higher infrared reflectance than the identification subject resin piece.

The conveyor 20 conveys the resin piece to a location under the infrared spectroscopy device 30 (a measurement region range). Here, as shown in FIG. 1, the resin piece contacts the first guide 21 or the second guide 22 while being conveyed under the infrared spectroscopy device 30. More specifically, when the resin piece contacts the first guide 21, a position thereof is shifted to a left side of the conveyor 20 in a conveyance direction, and when the resin piece contacts the second guide 22, the resin piece is aligned with a center of the conveyor 20 in the conveyance direction.

The infrared spectroscopy device 30 obtains infrared reflection spectra continuously in time series order by emitting infrared light at predetermined time intervals, regardless of whether or not a resin piece is present. In other words, when a resin piece is present in the measurement range at an infrared reflection spectrum acquisition timing, the infrared spectroscopy device 30 obtains an infrared reflection spectrum from the resin piece, and when a resin piece is not present, the infrared spectroscopy device 30 obtains an infrared reflection spectrum from the conveyor 20. Note that the fixed interval is preferably as short as possible.

The controller 40 obtains the infrared reflection spectra from the infrared spectroscopy device 30. When a measurement method applied by the infrared spectroscopy device 30 is a Fourier transform spectroscopy method, the controller 40 may obtain interferogram signals, which correspond to analog signals not yet subjected to a Fourier transform, from the infrared spectroscopy device 30 in time series order instead of the infrared reflection spectra, which are the results of the Fourier transform. In other words, a technical feature of the present invention is that a signal power determined using data in the vicinity of a center burst of an interferogram signal, i.e. without the need for a Fourier transform or large-scale data processing such as integration or averaging of an entire reflection region, can be used. As a result, effects to be described below are obtained, thereby imparting superiority to the present invention over the related art.

The infrared reflection intensity indicates a peak intensity of the infrared reflection spectrum. Further, in the following description, a difference value obtained by subtracting a minimum value of an amplitude of an interferogram signal obtained at each measurement point from a maximum value of the amplitude will be referred to as a peak-to-peak amplitude of the interferogram signal. The peak-to-peak amplitude of the interferogram signal takes a value that corresponds approximately to the infrared reflection intensity detected by the FT-IR detector. Therefore, the interferogram signal and the infrared reflection spectrum will be described hereafter as equivalent signals.

The controller 40 selects an infrared reflection spectrum or an interferogram signal suitable for determining the presence of a resin piece by analyzing a plurality of infrared reflection spectra or a plurality of interferogram signals obtained as measurement results, and determines the resin type by analyzing the selected infrared reflection spectrum or interferogram signal.

Further, the controller 40 controls an open/closed condition of the air valve 52 provided in the resin piece separating device 50 such that air in the air pipe 53 is discharged through an ejection port in the air gun 51. When the resin type determination result indicates a resin type not defined in advance, the controller 40 discharges air through the ejection port in the air gun 51 at a predetermined timing so that the resin piece is collected in the foreign substance collection container 60.

When the resin type determination result indicates a resin type defined in advance, on the other hand, the controller 40 does not discharge air from the air gun 51. As a result, the resin piece falls into the resin piece collection container 70 positioned at an end point of the conveyor, and is thus collected as is.

Figure 2:
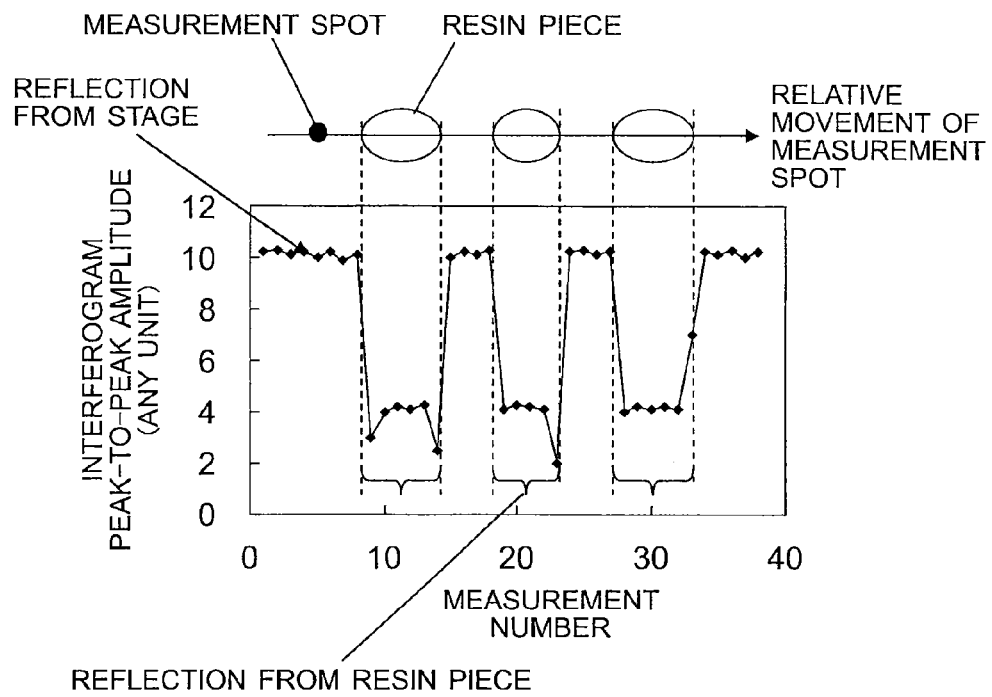
FIG. 2 is an illustrative view showing peak-to-peak amplitudes of interferogram signals obtained when FT-IR measurement is performed while moving a metal stage carrying resin pieces, according to the first embodiment of the present invention.

Next, a procedure for estimating a time at which a resin piece will arrive at a location in front of the ejection port of the air gun 51 by having the controller 40 analyze the infrared reflection spectrum or the interferogram signal will be described with reference to FIG. 2. FIG. 2 is an illustrative view showing the peak-to-peak amplitudes of interferogram signals obtained when FT-IR measurement is performed while moving a metal stage carrying resin pieces, according to the first embodiment of the present invention.

Here, to measure the peak-to-peak amplitudes of interferogram signals as shown in FIG. 2, three resin pieces having a flat portion (i.e. flattened resin pieces) are arranged on a metal stage corresponding to the conveyor 20 shown in FIG. 1, whereupon FT-IR measurement is performed at fixed intervals while moving the metal stage.

In this case, as shown in FIG. 2, a measurement spot serving as an infrared light emission range is fixed, and the metal stage moves through the measurement spot toward a left side of the paper surface. In other words, the measurement spot moves relative to the metal stage toward a right side of the paper surface. In the following description, it is assumed that the metal stage serves as a static system and the measurement spot moves relatively over the metal stage.

When a resin piece is present in the relatively moving measurement spot at the interferogram signal (infrared reflection spectrum) acquisition timing, the infrared spectroscopy device 30 obtains an interferogram signal reflected by the resin piece. When a resin piece is not present in the measurement spot, on the other hand, the infrared spectroscopy device 30 obtains an interferogram signal reflected by the metal stage.

In FIG. 2, the abscissa shows measurement numbers indicating an interferogram signal acquisition sequence starting from a first obtained interferogram signal. The measurement number corresponds to the timing (the time) at which the interferogram signal is obtained. Further, the ordinate shows the peak-to-peak amplitude of the interferogram signal corresponding to each measurement number (to be referred to simply as the peak-to-peak amplitude hereafter).

As described above, the peak-to-peak amplitude of the interferogram signal is a value corresponding approximately to the infrared reflection intensity detected by the FT-IR detector. Noise generated by a stochastic process can be relatively reduced with respect to a base line of the infrared reflection spectrum as the infrared reflection intensity increases. Therefore, when a peak signal that is generated by resin and has a high infrared reflection intensity is present, the S/N ratio relative to the peak signal is favorable, and as a result, determination errors during identification can be suppressed.

Here, as shown in FIG. 2, when an interferogram signal is obtained from the metal stage, the peak-to-peak amplitude is approximately 10. Note that this numerical value is a value limited to the present experiment system, and does not have any general significance in itself.

Further, three trough parts can be confirmed, and it is evident that the peak-to-peak amplitudes corresponding to the respective troughs are obtained from the three resin pieces arranged on the metal stage. The reason for this is that the infrared reflection intensity obtained from the resin pieces is smaller than the infrared reflection intensity obtained from the metal stage. Furthermore, when an interferogram signal is obtained from a resin piece, the peak-to-peak amplitude corresponding to a central portion (the flat portion) of the resin piece is approximately 4. In other words, as described above, when the conveyor 20 is constituted by a material having a greater infrared reflectance than the identification subject resin piece, the peak-to-peak amplitude corresponding to the conveyor 20 is larger than the peak-to-peak amplitude corresponding to the resin piece. A difference between the two peak-to-peak amplitudes is therefore clear, and as a result, an identification precision can be improved.

The peak-to-peak amplitudes corresponding to end portions of the respective resin pieces (measurement numbers 9, 14, 23) may be smaller than the peak-to-peak amplitudes corresponding to the flat portions. The reason for this is that the end portions of the resin pieces are not flat, and therefore a direction of infrared reflection light from the end portion of the resin piece deviates from a direction of the detector. The peak-to-peak amplitudes corresponding to the end portions of the respective resin pieces may also be larger (measurement number 33) than the peak-to-peak amplitudes corresponding to the flat portions. This occurs when a part of infrared reflection light from the metal stage becomes intermixed with the infrared reflection light from the end portion of the resin piece.

An intermediate value between the peak-to-peak amplitude corresponding to the metal stage and the peak-to-peak amplitude corresponding to the resin piece is 7 (=(10+4)/2). The following can be said in relation to measurement numbers where a value equal to or smaller than the intermediate value 7 can be obtained, assuming that an interferogram signal is obtained from the resin piece.

As shown in FIG. 2, the first resin piece exists in a range extending from a point (set as 8.5 here) between measurement numbers 8 and 9 to a point (set as 14.5 here) between measurement numbers 14 and 15. In this case, a center of the first resin piece is determined as 11.5 (=(8.5+14.5)/2).

Similarly, the second resin piece exists in a range extending from a point (18.5) between measurement numbers 18 and 19 to a point (23.5) between measurement numbers 23 and 24, and therefore a center of the second resin piece is determined as 21 (=(18.5+23.5)/2). Similarly again, the third resin piece exists in a range extending from a point (27.5) between measurement numbers 27 and 28 to the measurement number 33, and therefore a center of the third resin piece is determined as 30.25 (=(27.5+33)/2).

As described above, the measurement number corresponds to the interferogram signal acquisition timing (time), and therefore, when the central position of each resin piece is defined in association with a measurement number, the time at which the center of each resin piece passes the measurement spot can be estimated.

The time at which the center of the resin piece conveyed by the conveyor 20 in the configuration shown in FIG. 1 arrives at the measurement range (the measurement spot) can be estimated in a similar manner. By adding a movement time obtained by dividing a distance between the measurement range and the ejection port of the air gun 51 by a conveyance speed of the conveyor 20 to the arrival time at the measurement range, the time at which the resin piece arrives at the location in front of the ejection port of the air gun 51 can be estimated. Accordingly, the controller 40 can collect the resin piece in the foreign substance collection container 60 by discharging air from the air gun 51 at the estimated arrival time.

Figure 3:
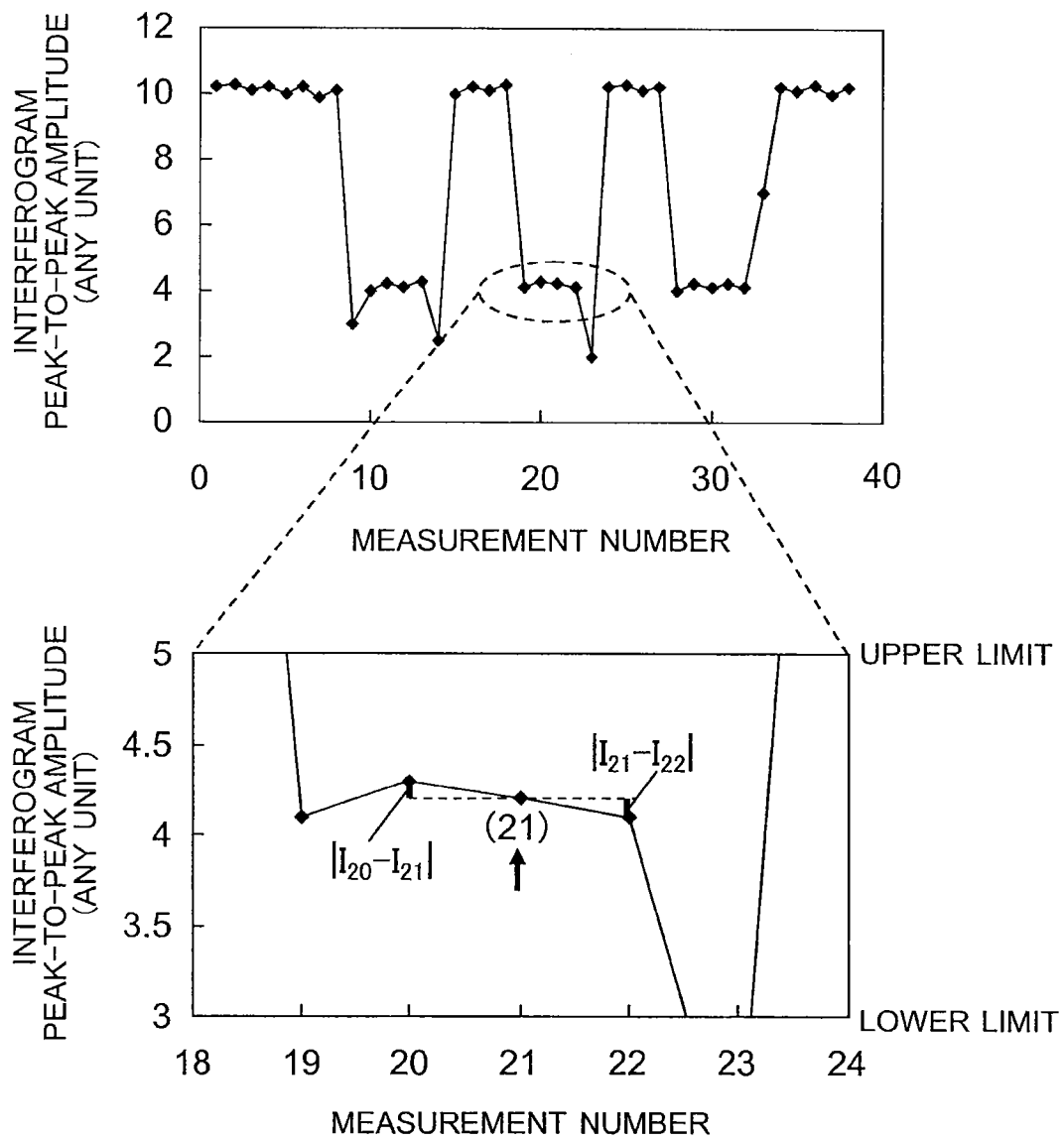
FIG. 3 is an illustrative view showing an example in which an infrared reflection spectrum to be used to identify a resin piece is selected from a plurality of infrared reflection spectra, according to the first embodiment of the present invention.

Next, selection of the infrared reflection spectrum used to identify the resin piece by means of interferogram signal analysis performed by the controller 40 will be described in detail with reference to FIGS. 2 and 3. FIG. 3 is an illustrative view showing an example in which the infrared reflection spectrum to be used to identify the resin piece is selected from a plurality of infrared reflection spectra, according to the first embodiment of the present invention.

Here, resin piece identification is performed on the basis of an infrared reflection spectrum obtained from the resin piece. However, the identification precision varies greatly according to the infrared reflection spectrum that is used for identification, from among a plurality of infrared reflection spectra obtained from a plurality of measurement points on a single resin piece.

An object of the present invention is to improve the precision with which a resin piece is identified by selecting the infrared reflection spectrum to be used for identification appropriately from respective infrared reflection spectra obtained at a plurality of measurement points.

Further, in the present invention, the controller 40 receives a signal power corresponding to an infrared reflection intensity from the infrared spectroscopy device 30 at predetermined time intervals in order to select the infrared reflection spectrum to be used for identification appropriately. A technical feature of the controller 40 is that the controller 40 selects at least one identifying signal power for identifying the resin type of the resin piece on the basis of respective magnitudes of the received signal powers by executing signal processing, and then selects the infrared reflection spectrum corresponding to the identifying signal power.

FIG. 3 corresponds to an enlarged view of a peak-to-peak amplitude corresponding to the vicinity (measurement numbers 18 to 24) of the second resin piece in FIG. 2. Here, as described above, when a larger peak-to-peak amplitude than the peak-to-peak amplitude corresponding to the resin piece is included, a part of the interferogram signal obtained from the metal stage is included. The infrared reflection spectrum corresponding to this peak-to-peak amplitude is preferably not used for identification. Further, when a smaller peak-to-peak amplitude than the peak-to-peak amplitude corresponding to the resin piece is included, the infrared reflection spectrum corresponding to the peak-to-peak amplitude has a poor S/N ratio and is therefore preferably not used for identification.

Hence, an upper limit value and a lower limit value of the peak-to-peak amplitude are defined in advance, and an infrared reflection spectrum corresponding to a peak-to-peak amplitude within a range of the upper limit value and the lower limit value (thresholds) is used for identification. Note that in FIGS. 3, 5 and 3 are used respectively as specific examples of the upper limit value and the lower limit value.

Next, a variation amount Δj is calculated in relation to a measurement number j, from among the measurement numbers within the predefined threshold range, in accordance with a following Equation (1). More specifically, a sum of an absolute value of a difference obtained by subtracting a peak-to-peak amplitude $I_j$ corresponding to the measurement number j from a peak-to-peak amplitude $I_{j-1}$ corresponding to a measurement number j−1 measured immediately before the measurement number j and an absolute value of a difference obtained by subtracting a peak-to-peak amplitude $I_{j+1}$ corresponding to a measurement number j+1 measured immediately after the measurement number j from the peak-to-peak amplitude corresponding to the measurement number j is calculated as the variation amount Δj.

$$\Delta j = -|I_{j-1} - I_j| + |I_j - I_{j+1}| \quad (1)$$

The variation amounts Δj of the respective measurement numbers are then compared, whereupon the infrared reflection spectrum corresponding to the measurement number at which the smallest variation amount Δj can be obtained is used to identify the resin piece. More specifically, an absolute value of an intensity difference with an adjacent peak-to-peak amplitude is calculated with respect to the peak-to-peak amplitude corresponding to each measurement number, and the infrared reflection spectrum corresponding to the measurement number at which a sum of the absolute values of the respective intensity differences is smallest is used.

In FIG. 3, as a specific example, a variation amount $\Delta j_{(j=21)}$ is calculated in accordance with Equation (1) with respect to a measurement number 21 (j=21), from among measurement numbers 19 to 22 corresponding to the peak-to-peak amplitudes within the range of the predefined thresholds (lower limit value 3 to upper limit value 5). More specifically, as shown in a following Equation (2), the controller 40 calculates a sum of an absolute value of a difference obtained by subtracting a peak-to-peak amplitude $I_{21}$ corresponding to the measurement number 21 from a peak-to-peak amplitude $I_{20}$ corresponding to a measurement number 20 measured immediately before the measurement number 21 and an absolute value of a difference obtained by subtracting a peak-to-peak amplitude $I_{22}$ corresponding to a measurement number 22 measured immediately after the measurement number 21 from the peak-to-peak amplitude $I_{21}$ corresponding to the measurement number 21 is calculated as the variation amount $\Delta j_{(j=21)}$.

$$\Delta j_{(j=21)} = |I_{20} - I_{21}| + |I_{21} - I_{22}| \quad (2)$$

The controller 40 calculates the variation amount Δj similarly in relation to the measurement numbers 19, 20, 22. The controller 40 then compares the respective variation amounts Δj at the measurement numbers 19 to 22, and uses the infrared reflection spectrum corresponding to the measurement number 21 at which the smallest variation amount $\Delta j_{(j=21)}$ can be obtained to identify the resin piece.

An identification method using the infrared reflection spectrum is performed in a following procedure, similarly to a conventional method. Data indicating a reference infrared reflection spectrum or a characteristic peak are obtained in advance in relation to each resin type, and the resin piece is identified by comparing the obtained data with the infrared reflection spectrum selected to identify the resin piece.

Hence, the controller 40 according to the first embodiment can calculate the variation amount Δj corresponding to each measurement number (each measurement position) in relation to the peak-to-peak amplitudes of a plurality of interferogram signals obtained from a single resin piece, and appropriately select the infrared reflection spectrum corresponding to the measurement number at which the smallest variation amount Δj can be obtained. As a result, the precision with which the resin piece is identified can be improved.

Figure 4:
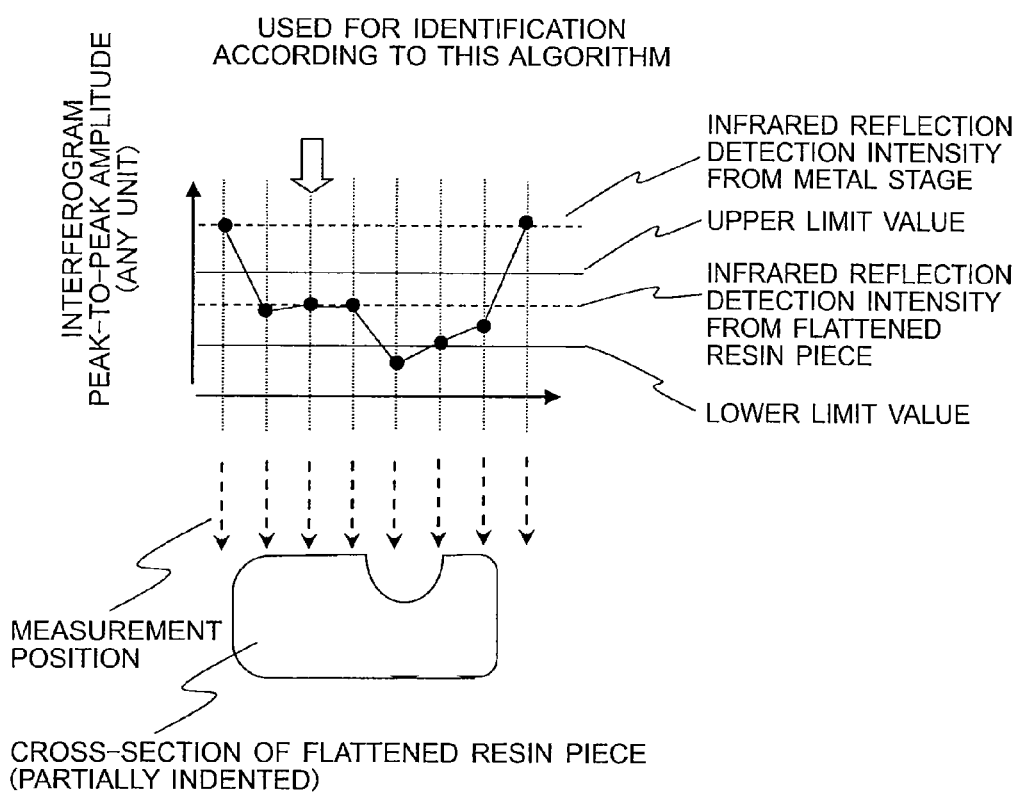
FIG. 4 is an illustrative view showing peak-to-peak amplitudes of interferogram signals measured in respective positions when a resin piece includes an indentation, according to the first embodiment of the present invention.

Another effect obtained by selecting the infrared reflection spectrum in the manner described above will now be described with reference to FIG. 4. FIG. 4 is an illustrative view showing the peak-to-peak amplitudes of the interferogram signals obtained in the respective measurement positions when the resin piece includes an indentation, according to the first embodiment of the present invention.

A resin piece having a flat surface without indentations was described in the above example, whereas here, an example of a case in which the surface of the resin piece includes a flat portion and an indentation will be described.

In this case, as shown in FIG. 4, similar variation to that of FIG. 2 is confirmed among the peak-to-peak amplitudes obtained from the flat portion of the resin piece, but the peak-to-peak amplitudes obtained from the vicinity of the indentation are smaller than those obtained from the flat portion. Therefore, when the infrared reflection spectrum is selected in the manner described above, the variation amounts Δj corresponding to the vicinity of the indentation are larger than the variation amounts Δj corresponding to the flat portion. Accordingly, the corresponding infrared reflection spectra are excluded from selection, and as a result, an infrared reflection spectrum from the flat portion is selected.

Hence, even when the resin piece includes an indentation, the selected infrared reflection spectrum is from the flat portion, and therefore identification can be performed with a low risk of a determination error. As a result, the precision with which the resin piece is identified can be improved.

Note that when a resin piece which is smaller than the FT-IR measurement region (in other words, a resin piece which is smaller than the fixed interval at which the infrared reflection spectra are obtained) exists among the identification subject resin pieces, it may be impossible to obtain an accurate infrared reflection spectrum, and therefore the peak-to-peak amplitude obtained from the resin piece may not be within the predefined thresholds. Hence, the configuration shown in FIG. 1 may further include a similar device to the resin piece separating device 50 and a collection container (not shown) so that when the controller 40 determines that a peak-to-peak amplitude obtained from a resin piece is not within the predefined thresholds and cannot therefore be identified, the resin piece determined to be unidentifiable can be collected.

Next, a case in which the infrared reflection spectrum is selected on the basis of a signal power other than the peak-to-peak amplitude of an interferogram signal will be described. As described above, the peak-to-peak amplitude of an interferogram signal takes a value that corresponds approximately to the infrared reflection intensity detected by the detector.

Instead of the peak-to-peak amplitude of an interferogram signal, a difference between an average value and a maximum value of the interferogram signal, a difference between the average value and a minimum value of the interferogram signal, and so on, for example, may be used as the signal power corresponding to the infrared reflection intensity.

Furthermore, a reflection intensity detected in accordance with an arbitrary wavelength (wave number) of an infrared reflection spectrum, a DC component of a signal output from the detector (light reception unit) before determining the amplitude intensity of the interferogram signal, an integrated value of a power spectrum, an intensity corresponding to an arbitrary wavelength (wave number) of the power spectrum (excluding wavelengths (wave numbers) having absorbance by water and atmospheric components such as carbon dioxide), and so on, for example, may be used as the signal power corresponding to the infrared reflection intensity.

A power spectrum is an actual signal strength distribution at each wavelength (wave number), and is affected by a wavelength distribution of the infrared light source, a reflectance wavelength distribution of the sample, a shape or a thickness of the sample, a wavelength dependence of a detection sensitivity of the detector, and so on.

These cited signal powers may be used as an alternative to the infrared reflection intensity in a similar manner to the peak-to-peak amplitude of the interferogram signal. Note that in the first embodiment and second to fifth embodiments to be described below, cases in which the peak-to-peak amplitude of the interferogram signal is used are described, but similar effects are obtained likewise when these other signal powers are used.

Furthermore, when the peak-to-peak amplitude of the interferogram signal or a signal power determined from the interferogram signal is used, Fourier transform processing is not required to derive the infrared reflection spectra not used to identify the resin piece, and therefore a calculation processing load exerted on the controller 40 can be lightened.

According to the first embodiment, described above, the variation amount Δj corresponding to each measurement number (each measurement position) is calculated with respect to signal powers corresponding to the infrared reflection intensity, in this case the peak-to-peak amplitudes of the plurality of interferogram signals obtained from the resin piece, whereupon the infrared reflection spectrum corresponding to the measurement number at which the smallest variation amount Δj can be obtained is selected. As a result, the precision with which the resin piece is identified can be improved, and accurate identification processing can be performed in succession on individual resin pieces.

In the first embodiment, a single infrared reflection spectrum is selected for use in identifying the resin piece, but a plurality of infrared reflection spectra may be selected and used to identify the resin piece.

In this case, the resin piece is identified using an average infrared reflection spectrum or an integrated infrared reflection spectrum, which is obtained by averaging or integrating a series of infrared reflection spectra in which the difference with the adjacent infrared reflection intensity is smaller than a preset fixed value.

Further, when the measurement method is a Fourier transform spectroscopy method, the resin piece is identified using an infrared reflection spectrum determined from an average interferogram signal or an integrated interferogram signal, which is obtained by averaging or integrating interferogram signals within a range where the difference with the adjacent infrared reflection intensity is smaller than a preset fixed value.

By averaging or integrating a plurality of infrared reflection spectra or a plurality of interferogram signals in this manner, an infrared reflection spectrum having a more favorable S/N ratio can be obtained, enabling a further improvement in the identification precision.

Second Embodiment

In a second embodiment of the present invention, a case in which the infrared reflection spectrum to be used to identify the resin piece is selected by executing different signal processing to the first embodiment will be described.

Figure 5A:
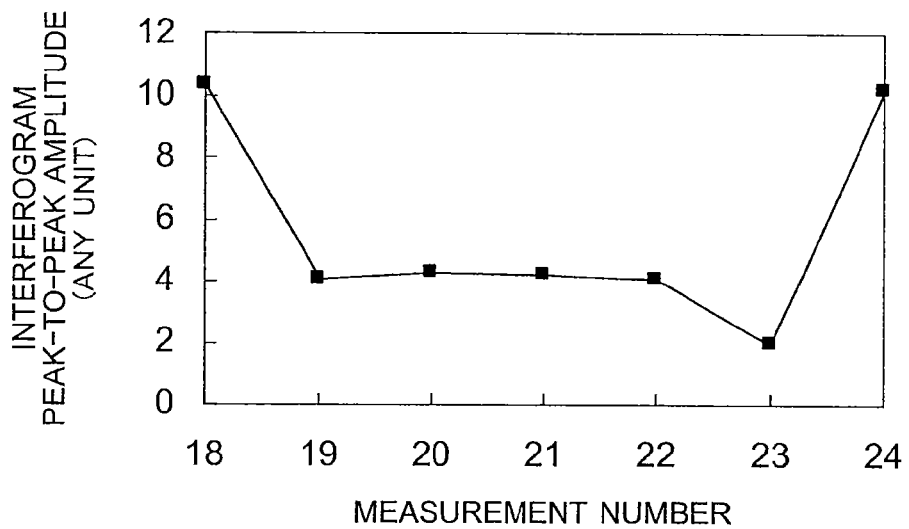
FIG. 5A is an illustrative view showing an example in which an infrared reflection spectrum to be used to identify a resin piece is selected from a plurality of infrared reflection spectra, according to a second embodiment of the present invention.
Figure 5B:
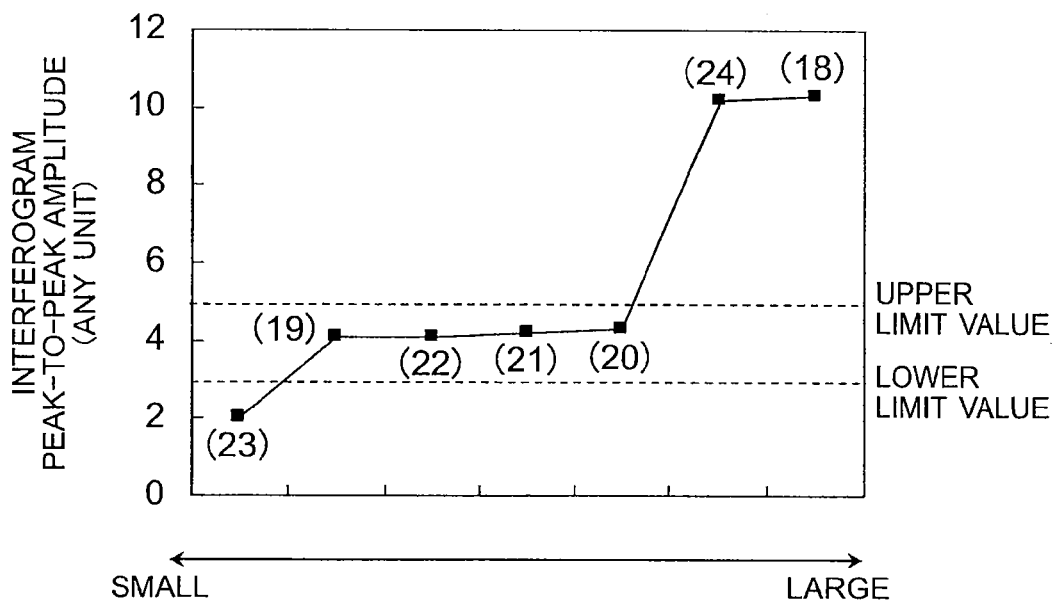
FIG. 5B is another illustrative view showing an example in which an infrared reflection spectrum to be used to identify a resin piece is selected from a plurality of infrared reflection spectra, according to the second embodiment of the present invention.

FIG. 5 is an illustrative view showing an example in which the infrared reflection spectrum to be used to identify the resin piece is selected from a plurality of infrared reflection spectra, according to the second embodiment of the present invention. FIG. 5A is an illustrative view showing peak-to-peak amplitudes corresponding to the vicinity of the second resin piece of FIG. 2 (measurement numbers 18 to 24), and FIG. 5B is an illustrative view showing a case in which the peak-to-peak amplitudes corresponding respectively to the measurement numbers 18 to 24 in FIG. 5A are rearranged into ascending order.

As shown in FIG. 5B, the peak-to-peak amplitudes corresponding respectively to the measurement numbers 18 to 24 are rearranged so as to increase steadily from left to right. For example, the peak-to-peak amplitude corresponding to the measurement number 23 is smallest and therefore shown on a left end, while the peak-to-peak amplitude corresponding to the measurement number 18 is largest and therefore shown on a right end.

Note that infrared reflection spectra corresponding to peak-to-peak amplitudes that are too small or too large are not suitable for identification. Similarly to the first embodiment, therefore, an upper limit value and a lower limit value of the peak-to-peak amplitude are defined in advance, and an infrared reflection spectrum corresponding to a peak-to-peak amplitude within the range of the upper limit value and the lower limit value (thresholds) is used for identification.

After rearranging the peak-to-peak amplitudes corresponding to the respective measurement numbers of the resin piece in this manner, an absolute value of an intensity difference with an adjacent peak-to-peak amplitude is calculated in relation to each measurement number within the range of the predefined thresholds. The infrared reflection spectrum corresponding to the measurement number at which a sum of the absolute value of the intensity difference with the peak-to-peak amplitude to the immediate right and the absolute value of the intensity difference with the peak-to-peak amplitude to the immediate left takes the smallest value is then used to identify the resin piece.

In a specific example shown in FIG. 5, the peak-to-peak amplitudes corresponding to the measurement numbers 18 to 24 are rearranged into ascending order, whereupon absolute values of the intensity difference with the adjacent peak-to-peak amplitude are calculated respectively in relation to the peak-to-peak amplitudes corresponding to the measurement numbers 19, 22, 21, 20 that are within the range of the predefined thresholds (lower limit value 3 to upper limit value 5).

According to the second embodiment, as described above, the peak-to-peak amplitudes corresponding to the respective measurement numbers (respective measurement positions) of the resin piece are rearranged into ascending order, whereupon the absolute values of the intensity difference with the adjacent peak-to-peak amplitude are calculated in relation to the peak-to-peak amplitudes corresponding to the respective measurement numbers. The infrared reflection spectrum corresponding to the measurement number at which the sum of the absolute values of the respective intensity differences takes the smallest value is then selected. In so doing, the precision with which the resin piece is identified can be improved, and moreover, an optimum infrared reflection spectrum for identification can be selected appropriately even when the infrared reflection intensity varies in the adjacent measurement position due to the formation of creases, undulations, and so on, for example, during the flattening processing for forming the flat portion on the surface of the identification subject resin piece.

Third Embodiment

In a third embodiment of the present invention, a case in which the infrared reflection spectrum to be used to identify the resin piece is selected by executing different signal processing to the first and second embodiments will be described. Note that in the third embodiment, it is assumed that the flat portion has been formed on the surface of the identification subject resin piece by flattening processing.

Figure 6:
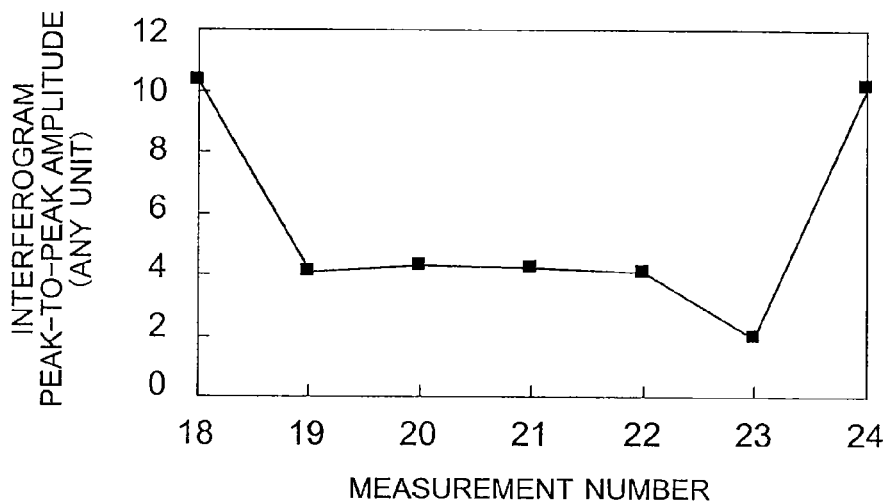
FIG. 6 is an illustrative view showing an example in which an infrared reflection spectrum to be used to identify a resin piece is selected from a plurality of infrared reflection spectra, according to a third embodiment of the present invention.

FIG. 6 is an illustrative view showing an example in which the infrared reflection spectrum to be used to identify the resin piece is selected from a plurality of infrared reflection spectra, according to the third embodiment of the present invention. FIG. 6 also shows the peak-to-peak amplitudes corresponding to the vicinity of the second resin piece of FIG. 2 (measurement numbers 18 to 24).

In FIG. 6, similarly to the first embodiment, the second resin piece exists within a range extending from a point (18.5) between the measurement numbers 18 and 19 to a point (23.5) between the measurement numbers 23 and 24. Further, the resin piece is identified using the infrared reflection spectrum corresponding to the measurement number at which the smallest value can be obtained from among the peak-to-peak amplitudes of the measurement numbers 19 to 23 corresponding to the second resin piece.

When the number of measurement numbers is three or more, the peak-to-peak amplitudes corresponding to the respective ends of the resin piece (in FIG. 6, the peak-to-peak amplitudes corresponding to the measurement numbers 19 and 23) are preferably excluded.

According to the third embodiment, described above, when the flat portion is formed on the surface of the resin piece by flattening processing, the infrared reflection spectrum corresponding to the measurement number at which the smallest value can be obtained from among the peak-to-peak amplitudes of the respective measurement numbers corresponding to the resin piece is selected. As a result, the infrared reflection spectrum that includes an infrared reflection signal generated by the resin piece, which is required for identification, and is least affected by infrared reflection signals generated by the conveyor is selected, and therefore the precision with which the resin piece is identified can be improved.

Fourth Embodiment

In a fourth embodiment of the present invention, a case in which the infrared reflection spectrum to be used to identify the resin piece is selected by executing different signal processing to the first to third embodiments will be described. Note that in the fourth embodiment, similarly to the third embodiment, it is assumed that the flat portion has been formed on the surface of the identification subject resin piece by flattening processing.

Figure 7:
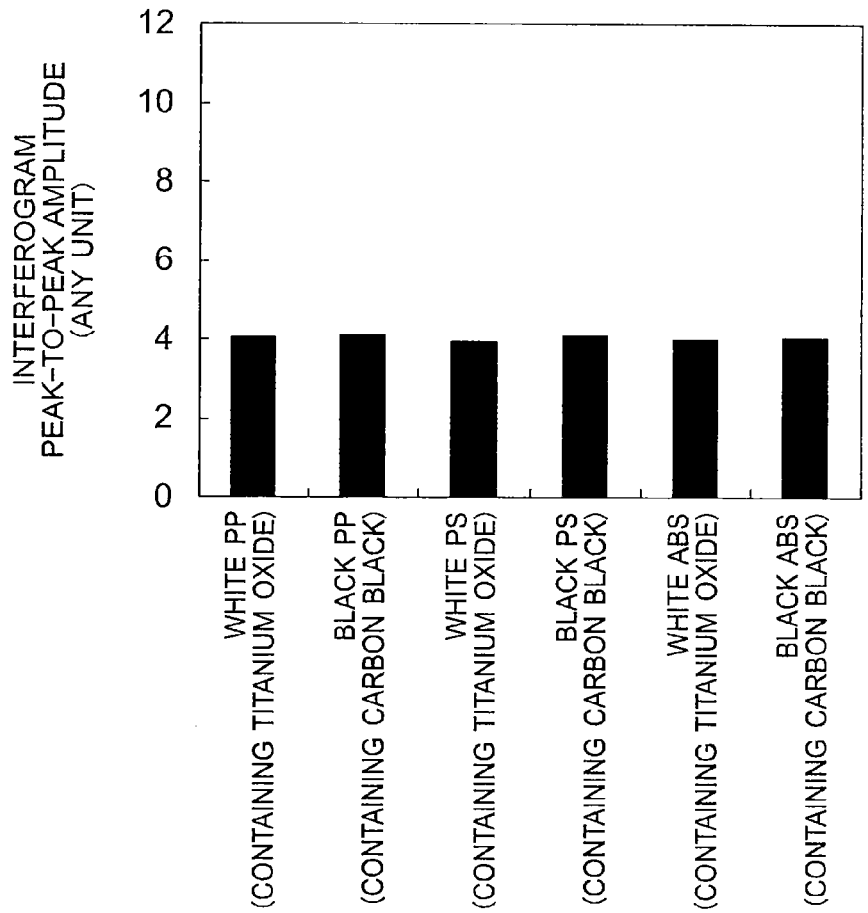
FIG. 7 is an illustrative view showing an example in which an infrared reflection spectrum to be used to identify a resin piece is selected from a plurality of infrared reflection spectra, according to a fourth embodiment of the present invention.

FIG. 7 is an illustrative view showing an example in which the infrared reflection spectrum to be used to identify the resin piece is selected from a plurality of infrared reflection spectra, according to the fourth embodiment of the present invention.

FIG. 7 shows respective peak-to-peak amplitudes of white PP (containing titanium oxide), black PP (containing carbon black), white PS (containing titanium oxide), black PS (containing carbon black), white ABS (containing titanium oxide), and black ABS (containing carbon black). These peak-to-peak amplitudes were obtained from the flat portions formed on the surfaces of the respective resin pieces by flattening processing.

Here, as is evident from FIG. 7, it was confirmed by experiment that when the resin pieces are flattened, the peak-to-peak amplitudes take substantially identical values (in FIG. 7, approximately 4) without being affected by differences in resin type or additives such as carbon filler.

Hence, a single peak-to-peak amplitude selected from the peak-to-peak amplitudes of the various flattened resin pieces is obtained in advance as a reference value, and during resin piece identification, the peak-to-peak amplitude that is closest to the reference value corresponding to the resin piece to be identified is selected from the plurality of actually obtained peak-to-peak amplitudes. The infrared reflection spectrum corresponding to the selected peak-to-peak amplitude is then selected as the infrared reflection spectrum to be used for identification.

Note that in consideration of long-term variation in the light source or the detector of the infrared spectroscopy device 30, a value normalized by the peak-to-peak amplitude corresponding to the conveyor 20 or the metal stage or a value normalized by an identical reference is preferably used as the reference value corresponding to the resin piece to be identified.

According to the fourth embodiment, as described above, when the flat portion is formed on the surface of the resin pieces by flattening processing, a single peak-to-peak amplitude selected from the peak-to-peak amplitudes of the various flattened resin pieces is obtained in advance as the reference value, and during resin piece identification, the infrared reflection spectrum corresponding to the peak-to-peak amplitude that is closest to the reference value corresponding to the resin piece to be identified is selected from the plurality of actually obtained peak-to-peak amplitudes. As a result, the precision with which the resin piece is identified can be improved.

Fifth Embodiment

In a fifth embodiment of the present invention, a case in which the infrared reflection spectrum to be used to identify the resin piece is selected by executing different signal processing to the first to fourth embodiments will be described.

Here, the upper limit value of the peak-to-peak amplitude is defined in advance, whereupon infrared reflection spectra corresponding respectively to a plurality of peak-to-peak amplitudes at or below the upper limit value are selected. Averaging processing or integration processing is then performed on the respective selected infrared reflection spectra to generate a single infrared reflection spectrum, and this spectrum is used to identify the resin piece.

Here, when the peak-to-peak amplitude is small, the infrared reflection signal generated by the resin piece is also small, but by subjecting a plurality of infrared reflection spectra to averaging processing or integration processing, the S/N ratio can be improved. When the peak-to-peak amplitude is large, however, this means that an infrared reflection signal generated by the conveyor is intermixed. Therefore, when the averaging processing or integration processing is performed on infrared reflection spectra including an infrared reflection spectrum corresponding to a large peak-to-peak amplitude, the S/N ratio deteriorates.

Hence, by performing the averaging processing or integration processing after selecting infrared reflection spectra corresponding respectively to a plurality of peak-to-peak amplitudes at or below the predefined upper limit value, the S/N ratio of the infrared reflection spectrum is prevented from deteriorating.

Further, a resin piece not subjected to flattening processing may include many irregularities and therefore have a low infrared reflection intensity, leading to a poor S/N ratio. Likewise in this case, however, by performing the averaging processing or integration processing on a plurality of infrared reflection spectra in a similar manner, the S/N ratio can be improved.

According to the fifth embodiment, as described above, the upper limit value of the peak-to-peak amplitude is defined in advance, infrared reflection spectra corresponding respectively to a plurality of peak-to-peak amplitudes at or below the predefined upper limit value are selected, and then averaging processing or integration processing is performed on the respective selected infrared reflection spectra to generate a single infrared reflection spectrum. As a result, the precision with which the resin piece is identified can be improved.

Note that in the fifth embodiment, a case in which averaging processing or integration processing is performed on the selected infrared reflection spectra was described, but the fifth embodiment is not limited thereto, and similar effects are obtained when a single interferogram signal is generated by performing averaging processing or integration processing on interferogram signals corresponding respectively to a plurality of peak-to-peak amplitudes at or below the predefined upper limit value, and an infrared reflection spectrum determined by subjecting the interferogram signal to a Fourier transform is used to identify the resin piece.

Sixth Embodiment

In a sixth embodiment of the present invention, a case in which the infrared reflection spectrum to be used to identify the resin piece is selected by executing different signal processing to the first to fifth embodiments will be described.

Here, similarly to the fifth embodiment, the upper limit value of the peak-to-peak amplitude is defined in advance, whereupon infrared reflection spectra corresponding respectively to a plurality of peak-to-peak amplitudes at or below the predefined upper limit value are selected. The resin piece is then identified by making an overall determination on the basis of the plurality of selected infrared reflection spectra.

More specifically, a score to be used for identification is calculated in relation to each of the plurality of selected infrared reflection spectra, whereupon a final score is calculated as a representative value of each score by performing statistical processing on the respective calculated scores of the infrared reflection spectra. The resin piece is then identified on the basis of the calculated final score.

Note that here, a method of determining a single representative value from a plurality of values such as the average, the mode, and the median, for example, is applied as the statistical processing.

In a specific example of resin piece identification, a score is calculated for each of a plurality of selected infrared reflection spectra such that ten scores, for example, are calculated. The statistical processing is then performed on the ten scores of the respective infrared reflection spectra in accordance with each score such that final scores (denoted here by S01, S02, . . . , S10) are calculated as representative values of the ten scores.

A score integration function V such as a function that returns a three-dimensional vector (Equation (3) below, for example) is then defined from the ten calculated scores, whereupon a value of V is calculated.

$$V = F(S01, S02, \ldots, S10) \tag{3}$$

In other words, during resin piece identification, V1 (PP), V2 (PS), and V3 (ABS) are calculated in accordance with Equation (3) as values of V corresponding to relationships between the resin piece to be identified and the reference resins (set here as PP resin, PS resin, and ABS resin). The resin having the highest score from among V1 (PP), V2 (PS), and V3 (ABS) is then determined to be the resin type of the resin piece to be identified.

Further, when a resin piece is identified by making an overall determination on the basis of a plurality of selected infrared reflection spectra, the resin piece may be identified using a following procedure instead of the procedure described above.

Similarities between the plurality of selected infrared reflection spectra and infrared reflection spectra corresponding to the reference resins are quantified and compared, whereupon the resin having the greatest similarity is determined to be the resin type of the resin piece to be identified.

Here, a method of determining standard deviations between measurement values and the reference samples at a plurality of specific wave numbers, for example, may be used as a method of quantifying the similarity. Note that a standard deviation takes a value within a range of −1 to 1, wherein a standard deviation of 1 indicates a perfect correlation and a standard deviation of 0 or less indicates no correlation or a negative correlation.

The standard deviations are calculated by comparing the infrared reflection spectra of the resin piece to be identified with the infrared reflection spectra of the reference resins, whereupon the resin having the standard deviation closest to 1 is determined to be the resin type of the resin piece to be identified.

For example, when three infrared reflection spectra are selected from a single resin piece, the similarities between a first infrared reflection spectrum and the infrared reflection spectra of the reference resins are 0.1 in the case of PP resin, 0.2 in the case of PS resin, and 0.3 in the case of ABS resin. Further, the similarities of a second infrared reflection spectrum are 0.05 in the case of PP resin, 0.2 in the case of PS resin, and 0.15 in the case of ABS resin, while the similarities of a third infrared reflection spectrum are 0.05 in the case of PP resin, 0.5 in the case of PS resin, and 0.2 in the case of ABS resin.

In this case, the resin having the greatest similarity, i.e. the similarity closest to 1, is the PS resin, to which the similarity of the third infrared reflection spectrum is 0.5, and therefore PS resin is determined to be the resin type of the resin piece to be identified.

A following method may be used as a different determination method. When the similarities of the three infrared reflection spectra to the PP resin, the PS resin, and the ABS resin are respectively integrated, a similarity of 0.2 (=0.1+0.05+0.05) is obtained with respect to the PP resin, a similarity of 0.9 (=0.2+0.2+0.5) is obtained with respect to the PS resin, and a similarity of 0.65 (=0.3+0.15+0.2) is obtained with respect to the ABS resin. Hence, PS resin, which has the greatest integrated similarity of 0.9, is determined to be the resin type of the resin piece to be identified. Note that performing averaging processing on the respective similarities of the three infrared reflection spectra instead of integration processing is substantially identical.

Here, a case in which three infrared reflection spectra are selected from a single resin piece was described, but when the number of selected infrared reflection spectra is large, respective central values (medians) or most frequent values (modes) may be used. An advantage of this type of method, which does not use a maximum value or does not use the maximum value alone, is that a close similarity may be obtained coincidentally from a noise signal of the infrared reflection spectrum, and therefore the resin piece can be identified accurately while avoiding this type of similarity.

Note that a covariance method, a method of least squares, a multivariate analysis method, or a method using a Mahalanobis distance or the like, for example, may be used instead of the method of determining the standard deviation as the method of quantifying the similarity of the infrared reflection spectra.

According to the sixth embodiment, described above, a plurality of infrared reflection spectra are selected from a single resin piece, the infrared reflection spectra of the reference resins are compared with the respective infrared reflection spectra, and the resin piece is identified on the basis of comparison results. As a result, the precision with which the resin piece is identified can be improved.

What is claimed is:

1. A resin type identification method for identifying a resin type of resin pieces conveyed in succession to a measurement range by having a controller execute signal processing on the basis of time-series signal powers corresponding to infrared reflection intensities obtained by emitting infrared light onto said measurement range at predetermined time intervals, said controller implementing:
    a selection step of selecting at least one identifying signal power for identifying the resin type of said resin pieces from said time-series signal powers corresponding to measurement position of said each resin piece conveyed in succession, on the basis of respective magnitudes of said time-series signal powers, the selection step selecting the at least one signal power within a predetermined threshold range defined in advance as said identifying signal power from said time-series signal powers corresponding to the measurement position of said each resin piece conveyed in succession; and
    an identification step of identifying the resin type of said resin pieces on the basis of an infrared reflection spectrum corresponding to said selected identifying signal power in the predetermined threshold range defined in advance.

2. The resin type identification method according to claim 1, wherein, in said selection step, signal powers within the predetermined threshold range defined in advance are extracted as in-predetermined range signal powers from said time-series signal powers corresponding to the measurement position of said each resin piece conveyed in succession,
    in relation to the measurement positions corresponding respectively to said extracted in-predetermined range signal powers, a sum of an absolute value of a difference between each signal power and a signal power obtained in an immediately preceding measurement position in time series order and an absolute value of a difference between each signal power and a signal power obtained in an immediately following measurement position in time series order is calculated, and
    a single in-predetermined range signal power corresponding to a measurement position in which said calculated sum has a smallest value is selected as said identifying signal power.

3. The resin type identification method according to claim 1, wherein, in said selection step, signal powers within the predetermined threshold range defined in advance are extracted as in-predetermined range signal powers from said time-series signal powers corresponding to the measurement position of said each resin piece conveyed in succession,
    in relation to the measurement positions corresponding respectively to said extracted in-predetermined range signal powers, a sum of an absolute value of a difference between each signal power and a signal power obtained in an immediately preceding measurement position in time series order and an absolute value of a difference between each signal power and a signal power obtained in an immediately following measurement position in time series order is calculated, and
    at least one in-predetermined range signal power corresponding to a measurement position in which said calculated sum is equal to or smaller than a predetermined value defined in advance is selected as said identifying signal power, and
    in said identification step, the resin type of said resin pieces is identified on the basis of a first infrared reflection spectrum generated by performing averaging processing or integration processing on respective infrared reflection spectra corresponding to said identifying signal powers selected in said selection step, or a second infrared reflection spectrum corresponding to a signal power generated by performing averaging processing or integration processing on said respective identifying signal powers selected in said selection step.

4. The resin type identification method according to claim 1, wherein, in said selection step, signal powers within the predetermined threshold range defined in advance are extracted as in-predetermined range signal powers from said time-series signal powers corresponding to the measurement position of said each resin piece conveyed in succession,
    said extracted in-predetermined range signal powers are rearranged into ascending order of magnitude,
    in relation to the measurement positions corresponding respectively to said in-predetermined range signal powers rearranged into ascending order, a sum of an absolute value of a difference between each signal power and a signal power obtained in an immediately preceding measurement position after the rearrangement and an absolute value of a difference between each signal power and a signal power obtained in an immediately following measurement position after the rearrangement is calculated, and
    a single in-predetermined range signal power corresponding to a measurement position in which said calculated sum has a smallest value is selected as said identifying signal power.

5. The resin type identification method according to claim 1, further comprising a flattening processing step of forming a flat portion on a measurement surface of said resin pieces,
    wherein, in said selection step, a smallest signal power is selected as said identifying signal power from said time-series signal powers corresponding to the measurement positions of said successively conveyed resin pieces in which the flat portion is formed on the measurement surface in said flattening processing step.

6. The resin type identification method according to claim 1, further comprising a flattening processing step of forming a flat portion on a measurement surface of said resin pieces,
wherein, in said selection step, a single signal power selected from respective signal powers corresponding to infrared reflection intensities obtained from various flattened sample resin pieces is defined in advance as a reference value, and
a signal power that is closest to said reference value is selected as said identifying signal power from said respective signal powers corresponding to the measurement positions of said successively conveyed resin pieces in which the flat portion is formed on the measurement surface in said flattening processing step.

7. The resin type identification method according to claim 1, wherein, in said selection step, at least one signal power within the predetermined threshold range defined in advance is selected as said identifying signal power from said time-series signal powers corresponding to the measurement position of said each resin piece conveyed in succession, and
in said identification step, the resin type of said resin pieces is identified on the basis of a first infrared reflection spectrum generated by performing averaging processing or integration processing on respective infrared reflection spectra corresponding to said identifying signal powers selected in said selection step, or a second infrared reflection spectrum corresponding to a signal power generated by performing averaging processing or integration processing on said respective identifying signal powers selected in said selection step.

8. The resin type identification method according to claim 1, wherein, in said selection step, at least one signal power within the predetermined threshold range defined in advance is selected as said identifying signal power from said time-series signal powers corresponding to the measurement position of said each resin piece conveyed in succession, and
in said identification step, the resin type of said resin pieces is identified on the basis of a final score obtained by calculating a score for use during identification in relation to respective infrared reflection spectra corresponding to said identifying signal powers selected in said selection step.

9. The resin type identification method according to claim 1, wherein, in said selection step, at least one signal power within the predetermined threshold range defined in advance is selected as said identifying signal power from said time-series signal powers corresponding to the measurement position of said each resin piece conveyed in succession, and
in said identification step, the resin type of said resin pieces is identified by quantifying and comparing similarities between respective infrared reflection spectra corresponding to said identifying signal powers selected in said selection step and infrared reflection spectra corresponding to reference resins.

10. The resin type identification method according to claim 1, further comprising a foreign substance separating step of separating a resin piece that is not of a predetermined resin type defined in advance as foreign substance when, in accordance with an identification result obtained in said identification step, said identified resin piece is not of said predetermined resin type.

11. The resin type identification method according to claim 2, further comprising a foreign substance separating step of separating a resin piece that is not of a predetermined resin type defined in advance as foreign substance when, in accordance with an identification result obtained in said identification step, said identified resin piece is not of said predetermined resin type.

12. The resin type identification method according to claim 3, further comprising a foreign substance separating step of separating a resin piece that is not of a predetermined resin type defined in advance as foreign substance when, in accordance with an identification result obtained in said identification step, said identified resin piece is not of said predetermined resin type.

13. The resin type identification method according to claim 4, further comprising a foreign substance separating step of separating a resin piece that is not of a predetermined resin type defined in advance as foreign substance when, in accordance with an identification result obtained in said identification step, said identified resin piece is not of said predetermined resin type.

14. The resin type identification method according to claim 5, further comprising a foreign substance separating step of separating a resin piece that is not of a predetermined resin type defined in advance as foreign substance when, in accordance with an identification result obtained in said identification step, said identified resin piece is not of said predetermined resin type.

15. The resin type identification method according to claim 6, further comprising a foreign substance separating step of separating a resin piece that is not of a predetermined resin type defined in advance as foreign substance when, in accordance with an identification result obtained in said identification step, said identified resin piece is not of said predetermined resin type.

16. The resin type identification method according to claim 7, further comprising a foreign substance separating step of separating a resin piece that is not of a predetermined resin type defined in advance as foreign substance when, in accordance with an identification result obtained in said identification step, said identified resin piece is not of said predetermined resin type.

17. The resin type identification method according to claim 8, further comprising a foreign substance separating step of separating a resin piece that is not of a predetermined resin type defined in advance as foreign substance when, in accordance with an identification result obtained in said identification step, said identified resin piece is not of said predetermined resin type.

18. The resin type identification method according to claim 9, further comprising a foreign substance separating step of separating a resin piece that is not of a predetermined resin type defined in advance as foreign substance when, in accordance with an identification result obtained in said identification step, said identified resin piece is not of said predetermined resin type.

19. The resin type identification method according to claim 1, wherein, in said selection step, signal powers within the predetermined threshold range defined in advance are extracted as in-predetermined range signal powers from said time-series signal powers corresponding to the measurement position of said each resin piece conveyed in succession,
in relation to the measurement positions corresponding respectively to said extracted in-predetermined range signal powers, a difference between each signal power and a signal power obtained in a preceding measurement position in time series order and a difference between each signal power and a signal power obtained in a following measurement position in time series order are calculated, and a single in-predetermined range signal power determined based on comparison of said calculated results is selected as said identifying signal power.

20. A resin type identification apparatus comprising:

an infrared spectroscopy device that obtains time-series signal powers corresponding to infrared reflection intensities by emitting infrared light onto a measurement range at predetermined time intervals;

a conveyor that conveys resin pieces in succession to said measurement range of said infrared spectroscopy device; and a controller that identifies a resin type of said resin pieces conveyed by said conveyor in succession to said measurement range, by executing signal processing on the basis of the time-series signal powers corresponding to said infrared reflection intensities received from said infrared spectroscopy device, wherein said controller selects at least one identifying signal power for identifying the resin type of said resin pieces from said time-series signal powers corresponding to measurement position of said each resin piece conveyed in succession, on the basis of respective magnitudes of said time-series signal powers and within a predetermined threshold range defined in advance as said identifying signal power from said time-series signal powers corresponding to the measurement position of said each resin piece conveyed in succession, and identifies the resin type of said resin pieces on the basis of an infrared reflection spectrum corresponding to said selected identifying signal power in the predetermined threshold range defined in advance.

21. The resin type identification apparatus according to claim 20, wherein said conveyor is constituted by a material having a greater infrared reflectance than said resin pieces.

\* \* \* \* \*